United States Patent [19]
Benton et al.

[11] Patent Number: 5,221,456
[45] Date of Patent: Jun. 22, 1993

[54] INSULATED CORE ELECTRODE FOR PH SENSOR

[75] Inventors: Barry W. Benton, Orange, Calif.; Lawrence R. Majerus, Chaska, Minn.; Donald R. Rutt, Eden Prairie, Minn.; Fred C. Sittler, Excelsior, Minn.; Adrian C. Toy, Eden Prairie, Minn.

[73] Assignee: Rosemount Inc., Minneapolis, Minn.

[21] Appl. No.: 781,106

[22] Filed: Oct. 22, 1991

[51] Int. Cl.[5] .......................................... G01N 27/26
[52] U.S. Cl. ................... 204/416; 204/418; 204/419; 204/433; 204/435
[58] Field of Search .......... 204/416, 433, 435, 243 R, 204/418, 419

[56] References Cited

U.S. PATENT DOCUMENTS

| | | | |
|---|---|---|---|
| 3,486,997 | 12/1969 | Petersen | 204/435 |
| 3,498,901 | 3/1970 | Metz et al. | 204/433 |
| 3,709,810 | 1/1973 | Grubb et al. | 204/433 |
| 4,133,735 | 1/1979 | Afromowitz et al. | 204/195 G |
| 4,547,272 | 10/1985 | Josefowicz | 204/243 R |
| 4,549,951 | 10/1985 | Knudson et al. | 204/416 |
| 4,595,487 | 6/1986 | Nunlist | 204/433 |
| 4,818,365 | 4/1989 | Kinlen et al. | 104/433 |
| 4,929,313 | 5/1990 | Wrighton | 104/153.1 |
| 5,078,854 | 1/1992 | Burgess et al. | 204/416 |

OTHER PUBLICATIONS

Article from Sensors and Actuators, "Electronic Semi-conducting Oxides as pH Sensors", Fog, 5 (1984) pp. 137-146.

Article from *Sensors and Actuators*, B1 (1990) pp. 293-297 entitled "Mechanistic and Response Studies of Iridium Oxide pH Sensors", by M. J. Tarlov et al.

*Primary Examiner*—T. Tung
*Assistant Examiner*—Bruce F. Bell
*Attorney, Agent, or Firm*—Kinney & Lange

[57] ABSTRACT

A pH sensor has a core of an electrochemically inert insulating or semi-conductive material, and is coated with an electrically conductive, electrochemically sensitive coating. The preferred core is insulating and made of alumina, with a thin coating of iridium oxide deposited over at least a portion of the outer surface of the core. The coating is carried to a surface remote from the sensing surface and is used for making electrically conductive connections that lead to remote circuitry. The core is made in a form that can be supported and held in an insulating, electrochemically inert, deformable material that is sealed around the outer surface of the coating on the core to prevent leakage of chemicals being sensed. The body also permits sealing quite easily onto access ports on which the sensor housing is mounted. Various connections to the electrode coating can be made quite easily to provide for a unique sensor assembly.

35 Claims, 5 Drawing Sheets

INSULATED CORE ELECTRODE FOR PH SENSOR

BACKGROUND OF THE INVENTION

The present invention relates to a pH sensitive electrode that has an electrochemically inactive and electrically insulating or semi-conductor core coated with a thin coating of electrochemically active electrode material, and supported in an elastomeric body that has an opening to leave a portion of the sensitive coating exposed to a chemical sample. A conductor carries the signal generated at the chemical coating interface to suitable circuitry and the entire electrode assembly can be mounted in an outer housing to form a pH sensor. Preferably the core is made of alumina and the coating is deposited iridium oxide.

In the prior art, various pH sensors have been advanced, using an electrochemically active material which may be in the form of a solid bar, a cap, a sleeve or the like, or which may be a metal-metal oxide type electrode where the active material is a coating on an electrically conductive substrate. Some electrochemical active coatings have been applied to flat insulating substrates, but the signal connections are difficult to make because the connections have to be made on the active face and then insulated and sealed to protect the connections from the sample gas or solution with a chemical resistant epoxy or other material.

Most prior art electrodes are adhesively bonded to an assembly body, and most adhesives either deteriorate with age or are very fragile. Minute leakage of the sample solution that is being tested to the back of the electrode and/or its electrical connection is not unusual and the leakage results in a loss of signal or the generation of an extraneous electrochemical signal. Many of the problems of sealing the coated core and maintaining a sealed conductor coating interface are solved with the present invention.

SUMMARY OF THE INVENTION

The present invention relates to a junction type insulating or semi-conductor core/metal oxide coating electrode for indicating electrochemical properties of a gas or liquid sample. The core is preferably formed into a generally spherical shape and coated with the electrochemically sensitive material. The coating is very thin but uniform, and is applied either by known depositing techniques or by using a bath in which the core is placed for deposition to form the outer coating. The use of a thin coating reduces waste of very expensive materials used for the coatings, and also simplifies the handling of the coating. It also greatly reduces the amount of any waste material that has to be disposed of.

The electrode preferably is made of a chemically inert, electrically insulating or semiconductor core, that is coated with the electrochemically active coating. Alumina is a preferred core material, and a deposited coating of iridium oxide on the alumina core has been found to work well.

The use of insulating or semi-conductor cores, which are not electrochemically active, reduces likelihood of erroneous signals from the use of a conductive core. If the coating has pin holes, scratches or other flaws, the sample can contact the core and cause problems In the present invention, the flaws do not cause serious problems.

The electrode is held in a chemically inert elastomeric body, in a cavity in the body which seals against the exterior surface of the electrode, to form an electrode assembly. The body has an opening through which the coating on the electrode is exposed to the chemical sample being sensed. A plug can be removed from the elastomeric insulating body and a conductive elastomer can be slipped into place to directly contact the coating on the core for forming electrical contacts to carry the signal caused by electrochemical activity, at the exposed portion of the coating.

The use of an insulating elastomeric (deformable) holder greatly aids in forming a seal against outer surfaces of the coating on the electrode core.

In one form of electrode holder, a chemically inert, deformable ferrule is used to engage the electrode and it is mounted in an outer housing which permits tightening the ferrule against the coating on the electrode to insure a tight seal. The holder using the tightenable ferrule permits quick changing of the ball (spherical) electrode.

Temperature sensitive elements can be incorporated into the electrode by utilizing an electrically insulating material case over the temperature sensitive element, which case then forms the electrode core. The electrochemically sensitive coating is deposited over the insulating case with a portion of the coating exposed to the chemical sample. A conductor is connected to the coating for carrying the signal generated at the chemical-coating interface. The conductors for the temperature sensor are separate from the conductor attached to the electrochemically sensitive coating. The entire assembly forms an electrode unit that has direct temperature sensing for determining the temperature in the sample area.

Alternately, a temperature sensor can be provided with a conductive outer case which contacts a portion of the coating of a separate electrode core so the conductive outer case forms part of the conductor.

Suitable conventional methods of depositing the electrochemically active coating onto a core can be utilized. For example, when using iridium oxide, sputtering has been found to be a satisfactory method of depositing the coating. The coating may take place in a reactive atmosphere over a substantial length of time so that a uniform, hard, well bonded coating is obtained.

Chemical baths also can be utilized for providing a coating onto the cores. The coating that is used does not have to coat all of the surfaces of the core, so long as the sensing portion that is exposed has the electrochemically reactive materials thereon, and so long as the coating extends to a portion of the core remote from the sensing portion. Electrical conductors are applied to the remote portions of the coating.

DESCRIPTION OF THE PREFERRED EMBODIMENTS

Figure 1:
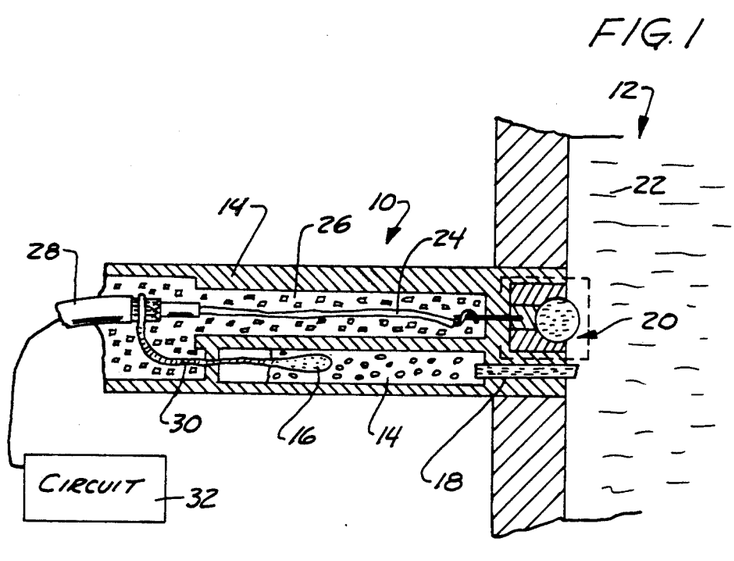
FIG. 1 is a schematic representation of a typical sensor utilizing an electrode assembly made according to the present invention.

Referring to FIG 1, a sensor indicated generally at 10 is used for sensing a desired electrochemically related property of a sample of a liquid (such as pH), which may be contained in a vessel as indicated generally at 12.

A sensor housing 14 has a number of interior chambers including a reference electrode chamber 15 that is filled with a reference electrolyte, and which houses a reference electrode 16. The reference electrolyte is in communication with the sample through a reference junction 18.

An electrode assembly 20 made according to the present invention is installed at the inner end of the sensor housing 14 and is positioned with a portion of a sensing electrode 34 exposed to the chemical sample indicated at 22 in the chamber 12. The electrode assembly 20 has a lead 24 from the sensing electrode 34, passing through a chamber 25 that is filled with an epoxy backfill indicated at 26 that is fluid tight and holds the lead 24 in position. The lead 24 then connects to a cable 28 that also includes a lead 30 from the reference electrode 16. The cable 28 is connected to suitable circuitry indicated at 32 for providing the information relating to the chemical sample 22 that is being sensed. The overall sensor housing, reference electrodes, and circuitry is well known, and is shown schematically for reference.

Figures 2, 3:
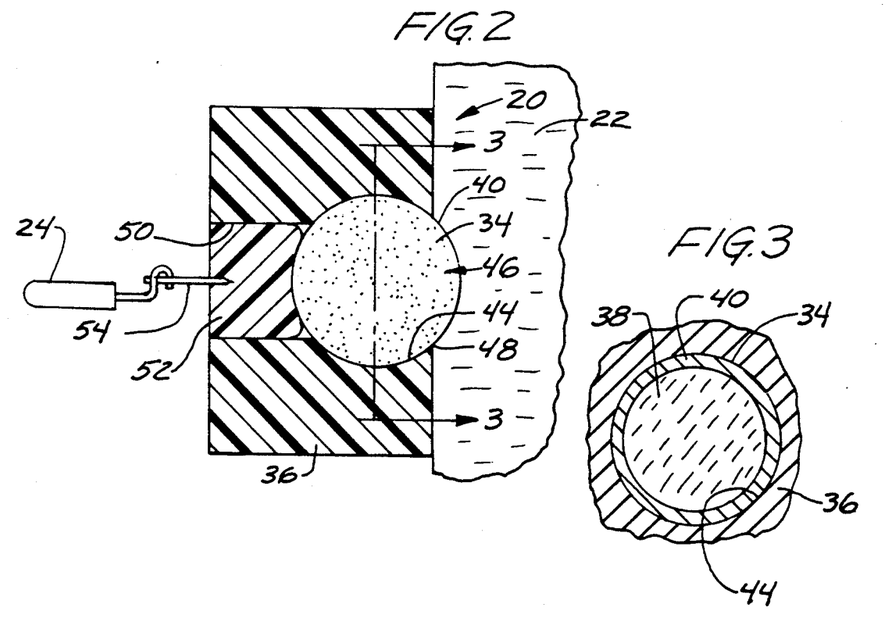
FIG. 2 is an enlarged sectional view of the electrode assembly used with the sensor of FIG. 1 and made according to the present invention.
FIG. 3 is a sectional view taken as on line 3—3 in FIG. 2.

The electrode assembly 20 made according to the present invention takes various forms. As shown in FIG. 2, a preferred form of the electrode assembly 20 comprises an insulator/metal oxide electrode 34 mounted in a body 36 to form the electrode assembly 20. As shown in FIG. 3, the electrode 34 comprises an electrode core member 38 that has a thin electrode coating 40 of an electrochemically sensitive material. The core 38 preferably is chemically inert, and electrically non-conductive, although electrically semiconductive material, such as silicon, also can serve as the core. Flat, wafer like electrodes made of a semi-conductor or an insulator, and having a deposited coating of electrochemically sensitive material can also be formed and have the advantages outlined above.

In the form shown in FIG. 3, the spherical electrode 34 is made by providing a spherical core 38, and then applying the coating 40 to desired portions of the exterior surface of the core. This application of the coating can be by sputtering in a reactive atmosphere, to form a metal oxide coating, or by using a coating bath.

Referring back to FIG. 2, the electrode body 36 is made of a chemically inert, electrically insulating elastomer that has a cavity 44 that receives a major portion of the electrode 34. The cavity 44 is made such that a sensing portion 46 of the electrode 34 is exposed to the chemical sample 22 and protrudes out of the body 36 through an opening indicated at 48. The elastomeric body 36 is formed so that it will tightly grip the outer surface of electrode 34 and retain the electrode 34 in place, and form a tight seal against the exterior surface of the coating 40.

In the form shown in FIG. 2, a plug, not shown, is removed from the body 36 to define a contact opening 50, and a quantity of conductive elastomeric material 52 is placed into the opening 50 and made to firmly contact the outer coating 40 of the electrode 34, to provide for an electrical contact. A lead or conductor indicated at 54 is connected to the conductive elastomeric contact material 52 either by bonding the lead 54 to an outer surface of material 52, as shown in FIG. 2, or alternatively, by piercing the material 52 with the lead 54 as shown in FIG. 1. Lead 54 is connected to lead 24, shown in FIG. 1, for carrying the signals indicating the electrochemical action on the coating 40.

The seal between the electrode 34 and the elastomeric body 36 is reliable and is easy to make. The elastomeric body 36 can be formed onto the electrode 34 while the electrode is held in a jig or fixture, so that there is tight adherence to the desired areas of electrode coating 40 while the sensing portion 46 remains uncovered. The body 36 can be tightened down onto the electrode for sealing with suitable clamping adjustments in the sensor housing 14.

The sensing portion 46 of the electrode may be covered, if desired, with a cured perfluorocarbon copolymer coating, to control migration of anions to the electrode, as is known. Perfluorocarbon co-polymers, such as those sold by E. I. DuPont under the trademark NAFION®, or by Dow Chemical under the trademark PFSA® are suitable.

Figure 4:
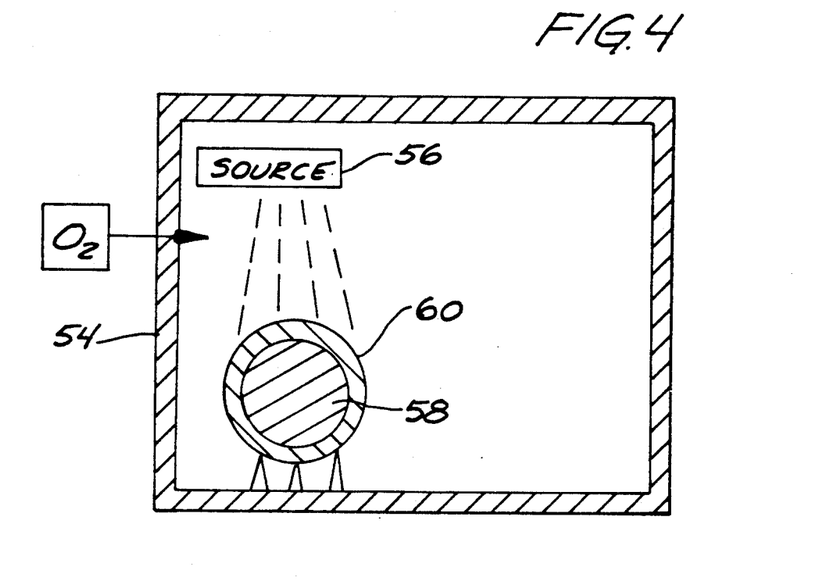
FIG. 4 is a schematic representation of a typical depositing chamber for sputtering iridium oxide onto an alumina substrate.

The preferred form of the substrate or core is an insulating ceramic material such as alumina ($Al_2O_3$) material that is formed in a desired spherical shape indicated at 58 in FIG. 4 and then is placed into a reactive chamber illustrated generally at 54 for sputter depositing from a source 56 in a normal manner. The coating indicated at 60 in FIG. 4, is then sputter deposited to the desired thickness in a reactive atmosphere. Iridium oxide is the preferred coating on the alumina core, and when an adequate thickness of the coating has been applied, the electrode will be removed and will be treated as desired for finishing.

Suitable semi-conductors, such as silicon, can be used for the core of the electrode, as well as insulating materials.

Figure 5:
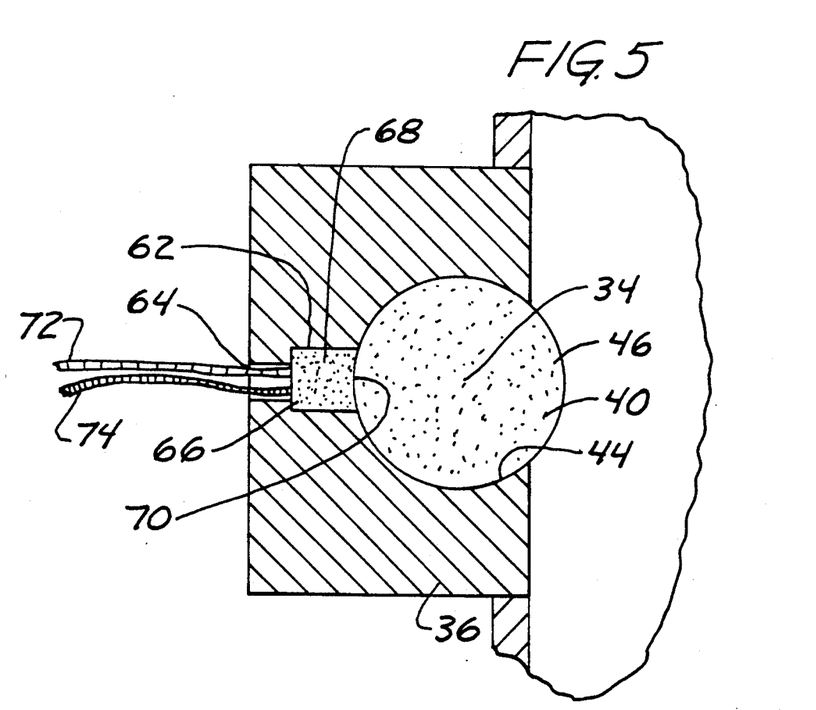
FIG. 5 is a modified form of the present invention showing a modified structure for making electrical contact to the coating on the core of the electrode assembly.

FIG. 5 shows an alternate form of the electrical contact. In this form of the invention, the body 36, and the electrode 34 are constructed in the same manner as previously described and the electrode 34 is placed into cavity 44 in the body 36. The body 36 is provided with a recess 62 leading from the cavity 44. Recess 62 connects to a passageway 64 that opens to the outside of the body 36. The recess 62 is sized to receive a temperature sensor shown 66, that can be a conventional temperature sensor such as a platinum resistance sensor, mounted in an insulating potting material and surrounded by a conductive case 68, that contacts the coating 40 of the electrode 34 in the region indicated at 70, and forms an electrical contact with the coating 40. Suitable lead 72 is connected to one end of the resistance sensor to provide a temperature signal, while a second lead 74 connects to the other end of the sensor and to the outer conductive housing 68 so that the signal generated by the presence of an electrolyte that causes a signal at the electrochemically active layer 40 is carried to suitable monitoring circuitry.

Figure 6:
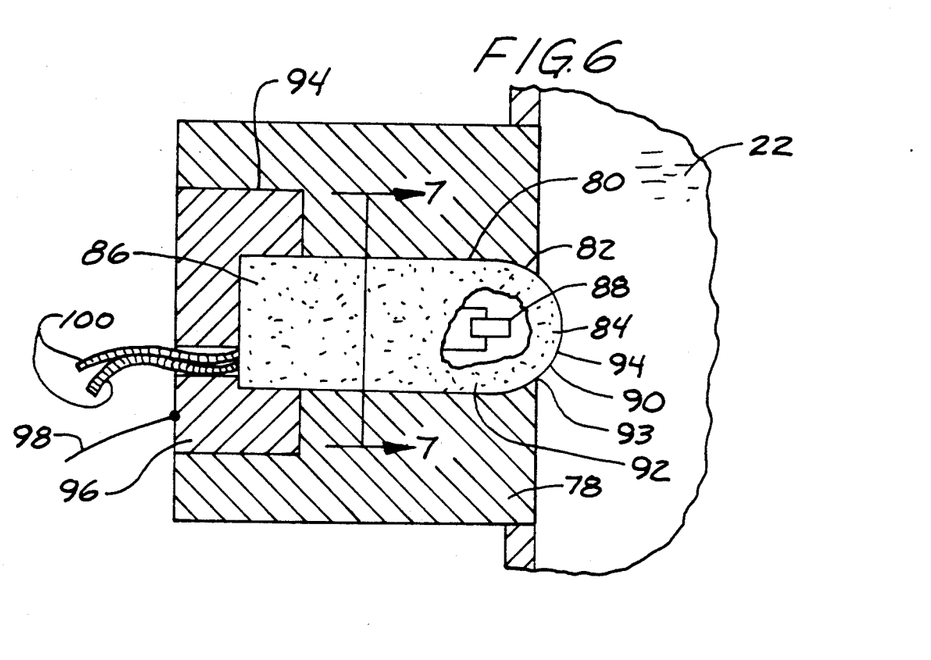
FIG. 6 is a further modified form of the invention illustrating a core made of an insulating case for temperature sensor.
Figure 7:
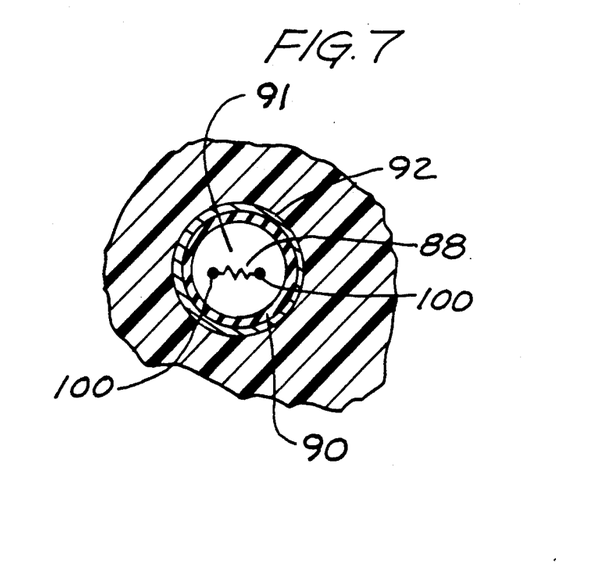
FIG. 7 is a sectional view taken generally on line 7—7 in FIG. 6.

A modified form of the invention is shown in FIG. 6, and in this instance, an insulating body 78 is formed to have a cylindrical cavity 80, with a rounded outer end portion 82 that will receive a hemispherical end 84 of an electrode 86. The electrode 86 is a combined temperature sensor and electrochemical activity sensing electrode, such as a pH sensor. In this form of the invention, a temperature sensor indicated at 88 (the outer case is partially broken away in FIG. 6) is formed on the interior of a hollow outer case 90 having hemispherical end 84. The case 90 is made of an insulating rigid material. As shown in FIG. 7, insulating material case 90 is tubular to house the sensor 88 which can be held in a potting compound 91. A suitable coating of electrochemically sensitive material 92 is provided on the case exterior surfaces of the case 90. A sensing portion 94 at the hemispherical end 84 is in the presence of the chemical sample 22 and protrudes out of a suitable opening 93 in the body 78.

The coating 92, which is electrically conductive and electrochemically sensitive, extends to a rear or remote portion of the electrode 86. A large counter bore 94 is provided at the remote end of the body 78, (remote from the chemical sample 22) and counter bore 94 is filled with an electrically conductive, elastomeric contact pad 96, that electrically connects to the coating 92. An electrical contact is secured to the conductive elastomer 96 for carrying the signal from sensing portion 94 to a lead 98. Suitable leads indicated at 100, are connected to the temperature sensor 88, and carry a temperature signal. In this form of the invention, the temperature signal can be used for determining the temperature of the chemical sample and the sensor body. The signal relating to the pH or other electrochemical activity is carried by the lead 98.

Figure 8:
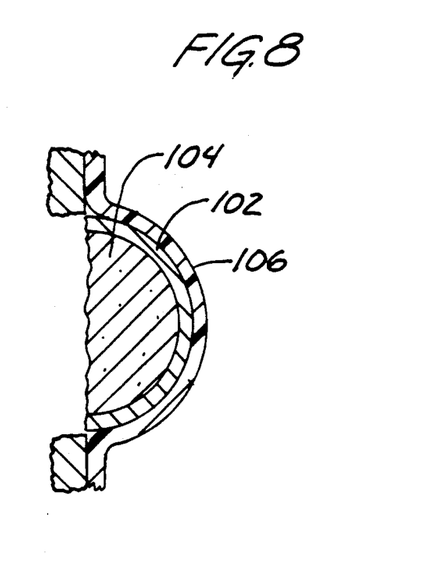
FIG. 8 is a sectional view through a sensing portion of the core and coating, showing a further semipermeable or permeable protective coating on the exterior of the electrochemically sensitive coating.

In FIG. 8, a sectional view of an electrode is shown, and a conductive, electrochemically active coating 102 is provided over an insulating or semiconductor body 104. An ion sensitive coating or layer is indicated at 106. Coating or layer 106 is a perfluorocarbon coating that permits transfer of cations to the chemically sensitive coating 102, but blocks anions from the coating 102. In some instances such an ion sensitive layer is desired, and it can be applied to the spherical electrode.

It should also be noted that the type of contact retainer shown in FIG. 5 can be used for holding contacts which are not temperature sensors. The shoulder of the recess 62 retaining the temperature sensor 66 provides a force urging the temperature sensor 66 against the coating 40 of the electrode 34 to make the electrical connection at the region 70. A flat disk can be held in the same manner by a shoulder in the housing 36 without having a temperature sensor in position. Spring loaded contacts also can be used for making the electrical connection to the electrochemically sensitive coating. It should also be noted that the coating on the core can be a semiconductive electrochemically sensitive coating. Whether or not there are fixture contact portions on the core surface that are not coated is not significant in operation, if the sensing portion of the electrode has the necessary coating and the core and coating are sealed tightly into the body 36.

The elastomeric body 36 is compressed by the sensor housing 14 when the sensor housing 14 is put into place as shown in FIG. 1. The compressed body 36 holds and seals the non-exposed portions of the coated electrode core, as well as provides a seal for the conductor 54 to prevent leakage of the sample into these sensitive areas.

The use of an exterior, ion sensitive membrane may be utilized on the sensor in the case of a pH sensor. If designed for an ORP (oxidation/reduction potential) sensor, the electrode would be formed by applying a platinum coating over a thermoplastic spherical core. The electrode opening in the body permits the electrode to be exposed to the sample to be sensed, while providing an adequate and reliable seal.

The core material may be a ceramic, as in the preferred embodiment of alumina, or thermoplastic, a thermo set insulating material, or a glass or a glassy ceramic sold under the trademark CERAM®. The core may be solid, hollow or a foamed material and may have a polished or textured surface. Any other surface treatment that is desired can be used. The core may be a dual purpose core as shown when a temperature sensitive element is housed in an insulating housing and coated with the electrochemically sensitive coating. Preferably the core is electrochemically inert, and an electrical insulator, although semi-conductors can also be used. The coating material that is electrochemically active, can be metals, metal oxides, combinations of them, or even a conductive polymer when used within the bodies shown that provide a seal. In addition to iridium, antimony, gold, lead, palladium, platinum, ruthenium, titanium, polyacitate, poly-p-phenylene, polytrimethyl-silylacetylene, silver, tantalum, and titanium, and oxides of those metals will work.

The cores used, as shown in FIG. 2, for the spherical electrode can be purchased in spherical form when made of alumina, and then cleaned and the electrochemically active coating can be deposited by sputtering in a reactive atmosphere. Uniform coating deposition, of course, is desired.

The advantage of an insulating or semiconducting core is that if pin holes develop, as may happen in thin, sputtered on coatings, there will not be a direct short between the electrolyte being sensed and the rest of the circuit through the conductive core.

The alumina substrate is prepared by soaking it in hot concentrated potassium-hydroxide (KOH) and then rinsing it in deionized water. After that, the cores are further rinsed and dried in a mechanical rinser/drier that is conventionally known. The iridium oxide is deposited by reactive sputtering from an iridium target in an oxygen atmosphere, as shown in FIG. 4. Slow deposition is preferred. The resulting electrode can be used without any overlying permeable coating or membrane, but a cured perfluorocarbon can be used as an exterior coating, and another type of coating that can be used is an epoxy amide film. The use of the exterior ion sensitive coating is optional.

Because the metal oxides layer can be reactively sputtered in place with no precursor, the insulating cores are successfully used. Also, the cores can be of a semi-conductor. The appropriate form or shape can be formed prior to reactive sputtering of an oxide coating and many of the advantages of an insulating core are present with a semi-conductor core. Pin holes, or thin spots or scratches in the coating will not cause inoperability, and the hard metal oxide coating is scratch resistant when placed onto a silicon base for example. A direct ohmic contact to the metal oxide is achieved through the silicon, and is available particularly in wafer form, as well as spherical form. Preferably, however, the electrode is formed into a spherical shape as shown at 110 in FIG. 9, which has a core 11 shaped by a reactive ion etch or other processes followed by an isotropic etch to smooth the surfaces. Core 111 of semi-conductor material is then stripped to bare silicon and may be doped to achieve substrate contact. The term non-conductive, as used herein, is intended to include semi-conductors.

The cores then can be placed into a sputtering chamber for reactive sputtering from a pure iridium target in an oxygen containing atmosphere, to form an iridium oxide layer 112 on the cores. As shown in FIG. 4, the cores can be supported on point type supports on the remote side of the electrode during sputtering.

Figures 9, 11:
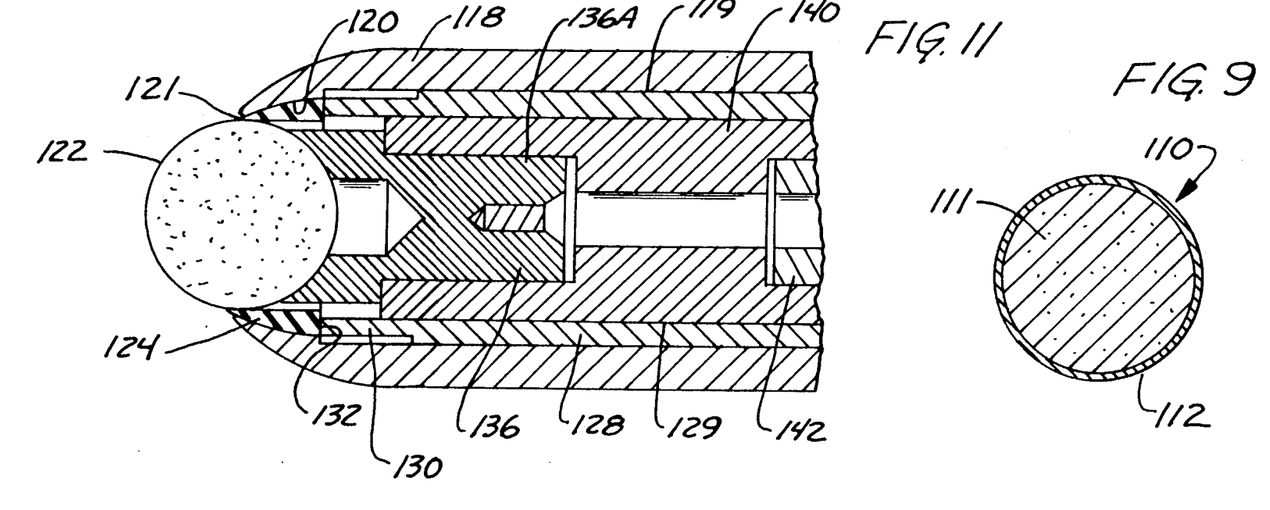
FIG. 9 is a cross section of an electrode made with a semi-conductor core.
FIG. 11 is an enlarged view of the electrode of FIG. 10 and an inert material ferrule used for holding the electrode in the assembly.
Figure 10:
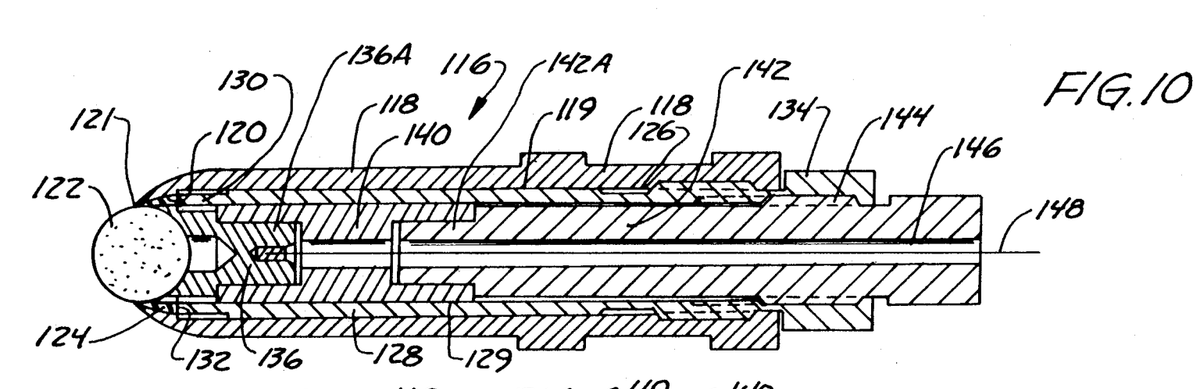
FIG. 10 is a cross sectional view of a modified electrode holder forming, with the electrode, an electrode assembly.

In FIGS. 10 and 11, a modified form of an electrode holder for a spherical electrode is utilized, which incorporates the use of a ferrule that surrounds and engages a spherical electrode, with a portion of the electrode protruding out of the ferrule, and which is mounted in an outer housing that can be used for tightening the ferrule down onto the surfaces of the electrode so that the electrode is positioned in a location where it can be placed into a solution to be tested, or exposed to such solutions through a suitable port.

As shown in FIG. 10, an electrode assembly indicated generally at 116 comprises an outer tubular housing 118, preferably made of stainless steel, and which has an inner bore 119 extending along its length. The housing 118 has cam or tapered inner surfaces indicated at 120 surrounding an end opening 121. The end opening 121 is tapered to permit a spherical (or part spherical) electrode 122 to protrude partially through the opening 121 to the exterior of the housing 118, as shown in FIGS. 10 and 11, and the inner cam surfaces 120 are used to guide, retain and tighten a ferrule 124 made of an inert deformable synthetic material and preferably a material such as tetrafluoroethylene, sold under the mark TEFLON that serves as a sleeve that can be tightened down around the surfaces of the spherical electrode 122 when the outer tapered or cam surfaces of the ferrule 124 are cammed against the surfaces 120. The ferrule size is selected so that its outer end would be just slightly smaller than the diameter of the spherical electrode 122, but would have a central bore that is just slightly larger than the spherical electrode 122 so that the electrode could be slipped into the ferrule 124 when desired.

The inner bore 119 of the housing 120 has a threaded outer end indicated at 126, and a ferrule retainer and pusher sleeve 128 is placed into the bore 119, as shown in FIG. 10. An inner end portion indicated at 130 of sleeve 128 is of slightly smaller diameter than the bore 119 and has an end surface shown at 132 that bears against an end surface of the ferrule 124.

The pusher sleeve 128 has external threads at its remote end that mate with the threads 126, and has an actuator end 134 that can be manually operated to thread the pusher sleeve 128 into place. When the ferrule 124 and the spherical ball 122 have been placed through the opening at 121 in the housing 118, the pusher sleeve 128 can be threaded into place and pressed against the ferrule 124 so that movement of the ferrule 124 will result and the ferrule 124 will be cammed by surfaces 120 and tightened down against the electrode surfaces to hold the electrode 122 in position partially protruding out of the housing 118. The ferrule material is positioned between the electrode 122 and the outer housing for sealing.

The tubular ferrule pusher or holder 128 also has a central bore 119 that receives a copper contact 136 that has an end surface formed generally spherically to engage the outer surface of the electrode 122 to form an electrical contact with the outer surface. The signal generated by the electrochemical reaction of the coating on the electrode 122 is carried by the copper contact 136. The contact 136 in turn is retained inside the pusher sleeve 12 by a isolator plug 140 that is made of a suitable insulating material, such as a plastic sold under the trademark LEXAN. The plug 140 has receptacles at opposite ends, one of which receives a tang portion 136A of the copper contact 136, and the other of which receives a tang portion 142A of a metal (aluminum) contact retainer. and pusher sleeve 142. The contact retainer 142 has outer threads 144 at its outer or remote end that mate with threads on the interior bore of the ferrule retainer and pusher sleeve 128. The contact retainer 142 also has a central bore 146 through which a lead wire 148 can pass. The lead wire 148 is electrically and mechanically attached or soldered to the copper contact 136 at the tang portion 136A of the copper contact.

The electrode assembly 116 thus forms a very convenient holder of spherical electrodes and incorporates the concept of utilizing a deformable material that is an insulator, chemically inert and which can grip on the outer surface of the spherical ball electrodes 122 to positively hold them in place.

This form of the invention has a holder body comprising of ferrule 124 that surrounds the electrode 122 for sealing purposes. The entire electrode assembly 116 can be mounted in suitable holders and the like for sealing against the leakage of the samples around the surfaces of the electrodes.

Figure 12:
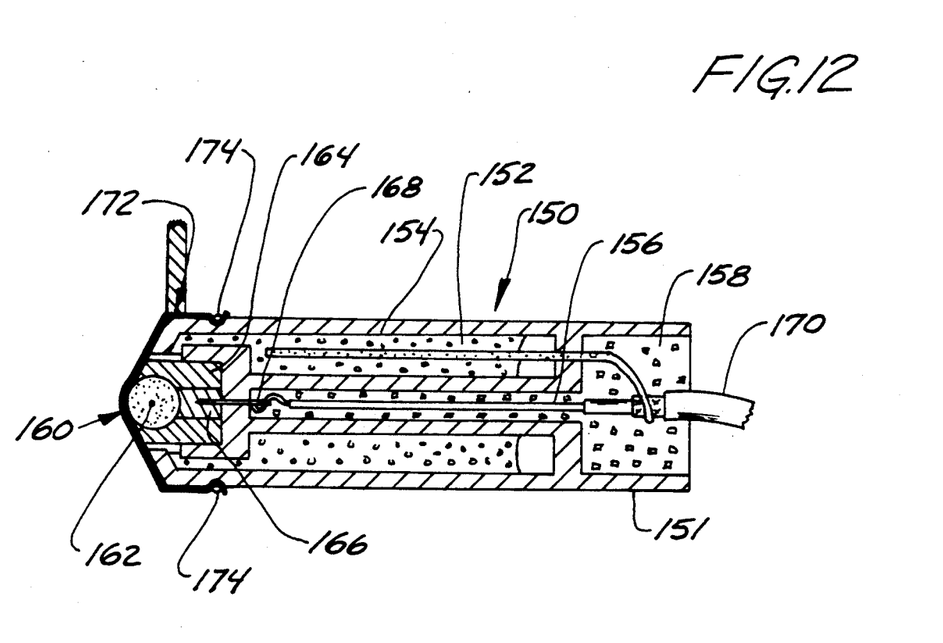
FIG. 12 is a sectional view of a sensor using a further modified form of the electrode of the present invention.

In FIG. 12, a modified form of the invention used in connection with a gas sensor having a permeable membrane on the housing is illustrated. The electrode assembly can be modified, but continues to utilize the insulating, electrode core having a suitable coating on the exterior. In this form of the invention, a gas sensor indicated generally 150 is shown, and includes a sensor housing 151 that has suitable passageways formed therein, and in this case where the gas sensor is utilized, an anode indicated at 152 is provided in a electrolyte 154 in one portion of the sensor housing 151. This electrolyte further fills the passageways surrounding a central bore 156 and a recessed chamber 158 at the outer end. The electrode assembly indicated generally at 160 comprises an electrode member 162 having an insulating core and coated with gold in this instance inasmuch as it is sensing a gas. The core can be an insulating ceramic material in this form of the invention, and the gold can be deposited on the core, in any desired manner. An elastomeric body of insulating, non-conductive and non-chemically reactive material indicated at 164 is used for supporting the electrode 162. A conductive elastomeric contact 166 is provided to the back side of the body 164 and connected to a suitable conductor 168 that is potted Within the central chamber or passageway 156 and extends outwardly through the chamber 158 to a lead wire 170. The anode 152 is also connected to the lead wire 170 to provide for the necessary signals carried along the lead 170.

In this form of the invention, a membrane indicated at 172 is placed over the electrode 162 and the sensing end of the housing 151 and is held in place with a suitable retainer ring 174, as shown. This semipermeable membrane permits gases to be sensed to pass through the membrane and contact the gold surface of the electrode 162 and a signal will be generated with respect to the anode 152 for providing information concerning the gas being sensed. This form of the invention is illustrated to show the different types of electrodes that can be made utilizing an insulating core, a coating of material that is suitable for providing an indication of contents of a gas or a liquid, and an insulating holder that is easily sealed around the surface of the electrode.

Although the present invention has been described with reference to preferred embodiments, workers skilled in the art will recognize that changes may be made in form and detail without departing from the spirit and scope of the invention.

We claim:

1. An indicator electrode assembly for sensing an electrochemical condition of a sample, the assembly comprising: a core of material that is chemically inert to the sample, a sensing portion comprising a coating of an electrochemically sensitive material placed on the core, a conductor electrically connected to the coating, and a body of an electrical insulating, electrochemically inert deformable material partially enveloping the core and the coating and having an opening of size to permit at least a portion of the sensing portion to be exposed by the body.

2. The indicator electrode assembly of claim 1, wherein the core is spherically shaped and is mounted in a part spherical opening in the body.

3. The indicator electrode assembly of claim 2 wherein the core is an insulating ceramic material, and the coating is iridium oxide.

4. The indicator electrode assembly of claim 3 wherein the core is ball shaped.

5. The indicator electrode assembly of claim 4 wherein the core is alumina.

6. The indicator electrode assembly of claim 4 wherein the core is a semi-conductor.

7. The indicator electrode assembly of claim 5 wherein the iridium oxide is sputter deposited onto the core.

8. The indicator electrode assembly of claim 1, wherein the coating extends to a side of the core remote from the opening in the body, and the conductor comprises a conductive polymer in contact with the coating.

9. The indicator electrode assembly of claim 1, and a temperature sensor mounted in a conductive sleeve, and means to hold the conductive sleeve in contact with the coating to form the conductor.

10. The indicator electrode assembly of claim 1 wherein the body of insulating, electromechanically inert deformable material comprises a ferrule having a central bore, and an end portion deformable toward the core and coating of an electrode, the electrode having at least a parts spherical surface that is engaged by he deformable end, the housing over said ferrule having a surface that engages the ferrule to urge the ferrule to deform against the core and coating and means to urge said ferrule against the portion of said housing.

11. The indicator electrode assembly of claim 10 and means supported relative to said housing to urge the electrode in the same direction as the direction of force acting to retain the ferrule.

12. The indicator electrode assembly of claim 11 wherein said means for urging the electrode includes a metal electrical conductor directly engaging the surface of the electrode and being urged against the electrode surface to form an electrical contact.

13. The indicator electrode assembly of claim 1 and an outer layer of an ion sensitive coating over the sensing portion and through which sample material passes to contact the coating.

14. An electrode assembly for indicating a condition of a sample comprising:
   a core member having at least a portion thereof forming a part spherical surface;
   a sensing portion on said part spherical surface having an exterior part spherical surface, the sensing portion comprising a coating of a selected material for sensing a condition of the sample;
   a conductor electrically connected to the coating;
   a sealing body engaging a portion of the exterior part spherical surface along a sealing line to define an exposed portion that is exterior of the sealing body; and
   said sealing body comprising a chemically inert, non-electrically conductive deformable material which prevents the sample to be sensed by the exposed portion from leaking past the sensing portion to the conductor.

15. The electrode assembly of claim 14, wherein said body forms a sleeve having a through opening, and one end of said opening having a camming surface defining an exterior thereof, and a housing around the sleeve having a mating interior camming surface, whereby when the sleeve and the housing are urged together so that their camming surfaces engage, the body is forced against the sensing portion in the through opening of the body.

16. The electrode assembly of claim 15 wherein said body comprises a block of an elastomeric material having a part spherical surface therein that mates with the exterior part spherical surface of the coating on the core and forms a seal therewith, and an outer housing for holding said body in position against the coating on the core.

17. The electrode assembly of claim 16 wherein said sensing portion has a cylindrical surface joining the exterior part spherical surface, said cylindrical surface being formed on a tube, and a temperature sensor on the interior of said tube, said tube being made of an insulating material.

18. The electrode assembly of claim 15 wherein said body comprises a ferrule and said housing is tubular and has a central opening, the electrode further comprising a ferrule pusher threadably mounted in said central opening and bearing against said ferrule to urge the camming surfaces together, said ferrule also being tubular, and a sensing portion pusher threadably mounted on the interior of said ferrule pusher and threadable relative to the ferrule pusher to urge the sensing portion in a direction toward the surface of the ferrule.

19. The electrode assembly of claim 18 wherein said sensing portion pusher comprises at least a section of an electrically insulating material, and the conductor directly engaging the coating to form electrical contact therewith.

20. The electrode assembly of claim 14 wherein the core member is an electrical insulator material.

21. The electrode assembly of claim 14 wherein the core member is a semi-conductor.

22. The electrode assembly of claim 16 wherein the coating on the core member is gold and a semi-permeable membrane covers the exposed portion of the sensing portion, the electrode sensing properties of ions passing through the membrane.

23. An indicator electrode for sensing the electrochemical condition of a sample, the indicator electrode comprising: a core of material that is chemically inert to the sample and having a partially spherical shaped surface, a sensing portion comprising a coating of an electrochemically sensitive material, directly deposited on the the partially spherical shaped surface to form a sensing surface for sensing electrochemical activity and, a conductor electrically connected to the coating.

24. The indicator electrode of claim 23 wherein the core is an insulating ceramic material, and the coating is iridium oxide sputtered on the core.

25. The indicator electrode of claim 24 wherein the core is alumina.

26. The indicator electrode of claim 23 wherein the coating is iridium oxide sputter deposited onto the core.

27. An assembly used to indicate a condition of electrochemical activity of a sample, the assembly comprising;
a sealing body having an opening leading to a cavity;
an electrode having an electrochemically sensitive outer coating wherein a portion of the outer coating is spherical, and wherein the electrode is disposed within the cavity such that a part of the spherical outer coating extends through the opening and is exposed to the sample, the sealing body engaging a portion of the spherical outer coating to make a seal therebetween to prevent the sample from entering the cavity; and
a conductor located within the cavity and electrically connected to the coating.

28. The assembly of claim 27 wherein the sealing body comprises a non-electrically conductive deformable material, and the assembly further comprises means for tightening the seal between the sealing body and the electrode.

29. The assembly of claim 28 and further comprising an outer housing having an opening defining inner camming surfaces, the electrode positioned within the opening with a portion of the electrode extending thereout, and the sealing body positioned between the electrode and the inner camming surfaces, and wherein the means for tightening comprises simultaneously urging the sealing body against the electrode and the inner camming surfaces.

30. The assembly of claim 29 wherein the sealing body comprises a ferrule, the housing is tubular and the means for tightening comprises a ferrule pusher threadably mounted within the housing to urge the sealing body against the electrode and the inner camming surfaces.

31. The assembly of claim 30 and further comprising an electrode pusher threadably mounted on the interior of the ferrule pusher to urge the electrode in a direction toward the ferrule.

32. The indicator electrode of claim 23 wherein the coating is a metal oxide.

33. The indicator electrode of claim 23 wherein the core is a semi-conductor.

34. The indicator electrode of claim 23 wherein the core is ball shaped.

35. The indicator electrode of claim 23 wherein the core has an inner cavity.

* * * * *

UNITED STATES PATENT AND TRADEMARK OFFICE
CERTIFICATE OF CORRECTION

PATENT NO. : 5,221,456
DATED : June 22, 1993
INVENTOR(S) : Benton et al.

It is certified that error appears in the above-indentified patent and that said Letters Patent is hereby corrected as shown below:

```
Col. 1 Line 39, delete "conductor coating",
                insert "conductor-coating"

Col. 7 Line 13, delete "11", insert "111"

Col. 9 Line 1, delete "Within", insert "within"

Col. 9 Line 66, delete "he", insert "the"
```

Signed and Sealed this

Fourth Day of October, 1994

BRUCE LEHMAN

Attest:

Attesting Officer

Commissioner of Patents and Trademarks